(12) United States Patent
Sharei et al.

(10) Patent No.: US 11,806,714 B2
(45) Date of Patent: *Nov. 7, 2023

(54) SELECTIVE DELIVERY OF MATERIAL TO CELLS

(71) Applicant: Massachusetts Institute of Technology, Cambridge, MA (US)

(72) Inventors: Armon R. Sharei, Cambridge, MA (US); Viktor A. Adalsteinsson, Cambridge, MA (US); Nahyun Cho, Closter, NJ (US); Robert S. Langer, Newton, MA (US); J. Christopher Love, Somerville, MA (US); Klavs F. Jensen, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 438 days.

This patent is subject to a terminal disclaimer.

(21) Appl. No.: 17/075,116

(22) Filed: Oct. 20, 2020

(65) Prior Publication Data

US 2021/0170411 A1 Jun. 10, 2021

Related U.S. Application Data

(63) Continuation of application No. 16/145,865, filed on Sep. 28, 2018, now Pat. No. 10,870,112, which is a (Continued)

(51) Int. Cl.
*B01L 3/00* (2006.01)
*C12N 5/09* (2010.01)
(Continued)

(52) U.S. Cl.
CPC ...... *B01L 3/502761* (2013.01); *C12N 5/0634* (2013.01); *C12N 5/0693* (2013.01);
(Continued)

(58) Field of Classification Search
CPC ....... B01L 3/502761; B01L 2200/0652; B01L 2300/08; B01L 2400/0487; C12N 5/0634;
(Continued)

(56) References Cited

U.S. PATENT DOCUMENTS 4,055,799 A 10/1977 Coster et al.
4,376,634 A 3/1983 Prior et al.
(Continued)

FOREIGN PATENT DOCUMENTS

CN 101031339 A 9/2007
CN 101031641 A 9/2007
(Continued)

OTHER PUBLICATIONS

Freitas Jr. Nanomedicine, vol. I: Basic Capabilities (1999), internet reprint, 1 page. (Year: 1999).*
(Continued)

*Primary Examiner* — Sean C. Barron
(74) *Attorney, Agent, or Firm* — Wolf, Greenfield & Sacks, P.C.

(57) ABSTRACT

Isolating or identifying a cell based on a physical property of said cell can include providing a cell suspension; passing said suspension through a microfluidic channel that includes a constriction; passing the cell suspension through the constriction; and, contacting said cell suspension solution with a compound. The constriction can be sized to preferentially deform a relatively larger cell compared to a relatively smaller cell.

21 Claims, 8 Drawing Sheets

Related U.S. Application Data continuation of application No. 14/912,001, filed as application No. PCT/US2014/051343 on Aug. 15, 2014, now Pat. No. 10,124,336.

(60) Provisional application No. 61/866,972, filed on Aug. 16, 2013.

(51) Int. Cl.

| | | |
|---|---|---|
| *C12N 5/078* | (2010.01) | |
| *G01N 15/14* | (2006.01) | |
| *C12Q 1/04* | (2006.01) | |
| *G01N 33/574* | (2006.01) | |
| *G01N 1/30* | (2006.01) | |
| *G01N 15/10* | (2006.01) | |
| *B82Y 30/00* | (2011.01) | |
| *C12M 3/06* | (2006.01) | |
| *G01N 15/00* | (2006.01) | |

(52) U.S. Cl.
CPC ........... *C12Q 1/04* (2013.01); *G01N 15/1459* (2013.01); *G01N 15/1484* (2013.01); *G01N 33/574* (2013.01); *B01L 2200/0652* (2013.01); *B01L 2300/08* (2013.01); *B01L 2400/0487* (2013.01); *B82Y 30/00* (2013.01); *C12M 23/16* (2013.01); *G01N 1/30* (2013.01); *G01N 2015/0065* (2013.01); *G01N 2015/1006* (2013.01); *G01N 2015/1081* (2013.01)

(58) Field of Classification Search
CPC .... C12N 5/0693; C12Q 1/04; G01N 15/1459; G01N 15/1484; G01N 33/574; G01N 1/30; G01N 2015/0065; G01N 2015/1006; G01N 2015/1081; B82Y 30/00

See application file for complete search history.

(56) References Cited

U.S. PATENT DOCUMENTS

| 4,835,457 | A | 5/1989 | Hanss et al. |
|---|---|---|---|
| 5,023,054 | A | 6/1991 | Sato et al. |
| 5,643,577 | A | 7/1997 | Pang et al. |
| 5,658,892 | A | 8/1997 | Flotte et al. |
| 5,842,787 | A | 12/1998 | Kopf-Sill et al. |
| 5,951,976 | A | 9/1999 | Segal |
| 6,133,503 | A | 10/2000 | Scheffler |
| 6,156,181 | A | 12/2000 | Parce et al. |
| 6,186,660 | B1 | 2/2001 | Kopf-Sill et al. |
| 6,218,166 | B1 | 4/2001 | Ravindranath et al. |
| 6,410,329 | B1 | 6/2002 | Hansen et al. |
| 6,461,867 | B1 | 10/2002 | Cai et al. |
| 6,562,616 | B1 | 5/2003 | Toner et al. |
| 7,109,034 | B2 | 9/2006 | Orwar et al. |
| 7,704,743 | B2 | 4/2010 | Fedorov et al. |
| 7,993,821 | B2 | 8/2011 | Chiu |
| 8,211,656 | B2 | 7/2012 | Hyde et al. |
| 8,669,044 | B2 | 3/2014 | Chiu |
| 8,679,751 | B2 | 3/2014 | Huang |
| 8,697,359 | B1 | 4/2014 | Zhang |
| 8,844,570 | B2 | 9/2014 | Glick |
| 9,005,579 | B2 | 4/2015 | Nowinski et al. |
| 9,017,991 | B2 | 4/2015 | Diefenbach |
| 9,157,550 | B2 | 10/2015 | Wheeler et al. |
| 9,255,245 | B2 | 2/2016 | Bernick et al. |
| 9,364,504 | B2 | 6/2016 | Godfrin et al. |
| 9,458,489 | B2 | 10/2016 | Lim et al. |
| 9,526,823 | B2 | 12/2016 | Yoshioka |
| 9,950,049 | B2 | 4/2018 | Godfrin et al. |
| 10,124,336 | B2 | 11/2018 | Sharei et al. |
| 10,526,573 | B2 | 1/2020 | Ding et al. |
| 10,696,944 | B2 | 6/2020 | Sharei et al. |
| 10,870,112 | B2 | 12/2020 | Sharei et al. |
| 11,111,472 | B2 | 9/2021 | Sharei et al. |
| 11,125,739 | B2 | 9/2021 | Sharei et al. |
| 11,299,698 | B2 | 4/2022 | Sharei et al. |
| 2003/0133922 | A1 | 7/2003 | Kasha, Jr. |
| 2004/0176282 | A1 | 9/2004 | Dalby et al. |
| 2004/0197898 | A1 | 10/2004 | Nakatani et al. |
| 2005/0026283 | A1 | 2/2005 | Ormar et al. |
| 2006/0134067 | A1 | 6/2006 | Liu et al. |
| 2006/0134772 | A1 | 6/2006 | Miles et al. |
| 2006/0223185 | A1 | 10/2006 | Fedorov et al. |
| 2007/0243523 | A1 | 10/2007 | Ionescu-Zanetti et al. |
| 2007/0249038 | A1 | 10/2007 | Adamo et al. |
| 2008/0026465 | A1 | 1/2008 | Nakata |
| 2008/0241844 | A1 | 10/2008 | Kellogg |
| 2008/0311140 | A1 | 12/2008 | Lee et al. |
| 2008/0318324 | A1 | 12/2008 | Chiu et al. |
| 2009/0209039 | A1 | 8/2009 | Adamo et al. |
| 2009/0280518 | A1 | 11/2009 | Adamo et al. |
| 2010/0203068 | A1 | 8/2010 | Betz et al. |
| 2010/0249621 | A1 | 9/2010 | Ichitani et al. |
| 2010/0323388 | A1 | 12/2010 | Chiu et al. |
| 2011/0014616 | A1 | 1/2011 | Holmes et al. |
| 2011/0030808 | A1 | 2/2011 | Chiou et al. |
| 2011/0091973 | A1 | 4/2011 | Glaser |
| 2011/0300205 | A1 | 12/2011 | Geall et al. |
| 2012/0064505 | A1 | 3/2012 | Suresh et al. |
| 2012/0107925 | A1 | 5/2012 | Li et al. |
| 2012/0207745 | A1 | 8/2012 | Godfrin et al. |
| 2012/0222143 | A1 | 8/2012 | Fahrenkrug et al. |
| 2013/0023051 | A1 | 1/2013 | Bundock et al. |
| 2013/0045211 | A1 | 2/2013 | Nowinski |
| 2013/0065314 | A1 | 3/2013 | MacMillan |
| 2014/0011226 | A1 | 1/2014 | Bernick et al. |
| 2014/0273229 | A1 | 9/2014 | Meacham et al. |
| 2014/0287509 | A1 | 9/2014 | Sharei et al. |
| 2015/0184127 | A1 | 7/2015 | White et al. |
| 2015/0196913 | A1 | 7/2015 | Liu |
| 2016/0017340 | A1 | 1/2016 | Wu |
| 2016/0193605 | A1 | 7/2016 | Sharei et al. |
| 2016/0199837 | A1 | 7/2016 | Breinlinger et al. |
| 2017/0020926 | A1 | 1/2017 | Mata-Fink et al. |
| 2017/0326213 | A1 | 11/2017 | Jajosky et al. |
| 2018/0003696 | A1 | 1/2018 | Sharei et al. |
| 2018/0016539 | A1 | 1/2018 | Ding et al. |
| 2018/0085402 | A1 | 3/2018 | Kahvejian et al. |
| 2018/0142198 | A1 | 5/2018 | Sharei et al. |
| 2018/0201889 | A1 | 7/2018 | Sharei et al. |
| 2018/0245089 | A1 | 8/2018 | Sharei et al. |
| 2019/0017072 | A1 | 1/2019 | Ditommaso et al. |
| 2019/0030536 | A1 | 1/2019 | Sharei et al. |
| 2019/0093073 | A1 | 3/2019 | Sharei et al. |
| 2019/0111082 | A1 | 4/2019 | Gilbert et al. |
| 2019/0382796 | A1 | 12/2019 | Gilbert et al. |
| 2020/0277566 | A1 | 9/2020 | Sharei et al. |
| 2021/0138050 | A1 | 5/2021 | Loughhead et al. |
| 2022/0064584 | A1 | 3/2022 | Sharei et al. |
| 2022/0091099 | A1 | 3/2022 | Sharei et al. |
| 2022/0195364 | A1 | 6/2022 | Sharei et al. |

FOREIGN PATENT DOCUMENTS

| CN | 106244543 A | 12/2016 |
|---|---|---|
| EP | 882448 A1 | 12/1998 |
| EP | 1225228 A2 | 7/2002 |
| EP | 2169070 A1 | 3/2010 |
| JP | H01-196566 A | 8/1989 |
| JP | H03-257366 A | 11/1991 |
| JP | 2010-025852 A | 2/2010 |
| JP | 2011-163830 A | 8/2011 |
| JP | 2013-536848 A | 9/2013 |
| JP | 6235085 B2 | 11/2017 |
| KR | 100760309 B1 | 10/2007 |
| KR | 100891487 B1 | 4/2009 |
| KR | 20110009422 A | 1/2011 |
| KR | 2014-0115560 A | 10/2014 |
| KR | 20140134524 A | 11/2014 |
| WO | WO 85/00748 A1 | 2/1985 |
| WO | WO 97/20570 A1 | 6/1997 |

(56) References Cited

FOREIGN PATENT DOCUMENTS

| | | |
|---|---|---|
| WO | WO 00/07630 A1 | 2/2000 |
| WO | WO 02/67863 A2 | 9/2002 |
| WO | WO 03/20039 A1 | 3/2003 |
| WO | WO 2004/001424 A1 | 12/2003 |
| WO | WO 2006/010521 A1 | 2/2006 |
| WO | WO 2006/095330 A2 | 9/2006 |
| WO | WO 2006/105251 A2 | 10/2006 |
| WO | WO 2007/067032 A1 | 6/2007 |
| WO | WO 2007/097934 A2 | 8/2007 |
| WO | WO 2008/021465 A2 | 2/2008 |
| WO | WO 2009/056332 A1 | 5/2009 |
| WO | WO 2010/016800 A1 | 2/2010 |
| WO | WO 2010/077290 A1 | 7/2010 |
| WO | WO 2010/105135 A1 | 9/2010 |
| WO | WO 2010/129671 A2 | 11/2010 |
| WO | WO 2010/145849 A2 | 12/2010 |
| WO | WO 2011/051346 A1 | 5/2011 |
| WO | WO 2011/119492 A2 | 9/2011 |
| WO | WO 2012/069568 A2 | 5/2012 |
| WO | WO 2012/097450 A1 | 7/2012 |
| WO | WO 2012/106536 A2 | 8/2012 |
| WO | WO 2012/118799 A2 | 9/2012 |
| WO | WO 2012/162779 A1 | 12/2012 |
| WO | WO 2013/059343 A1 | 4/2013 |
| WO | WO 2013/185032 A1 | 12/2013 |
| WO | WO 2014/065596 A1 | 5/2014 |
| WO | WO 2014/106629 A1 | 7/2014 |
| WO | WO 2014/106631 A1 | 7/2014 |
| WO | WO 2014/120956 A1 | 8/2014 |
| WO | WO 2014/165707 A2 | 10/2014 |
| WO | WO 2015/023982 A1 | 2/2015 |
| WO | WO 2015/061458 A1 | 4/2015 |
| WO | WO 2015/153102 A1 | 10/2015 |
| WO | WO 2015/161276 A2 | 10/2015 |
| WO | WO 2016/003485 A1 | 1/2016 |
| WO | WO 2016/070136 A1 | 5/2016 |
| WO | WO 2016/077761 A1 | 5/2016 |
| WO | WO 2016/109864 A1 | 7/2016 |
| WO | WO 2016/115179 A1 | 7/2016 |
| WO | WO 2016/183482 A1 | 11/2016 |
| WO | WO 2017/005700 A1 | 1/2017 |
| WO | WO 2017/008063 A1 | 1/2017 |
| WO | WO 2017/041050 A1 | 3/2017 |
| WO | WO 2017/041051 A1 | 3/2017 |
| WO | WO 2017/106899 A2 | 6/2017 |
| WO | WO 2017/123644 A1 | 7/2017 |
| WO | WO 2017/123646 A1 | 7/2017 |
| WO | WO 2017/123663 A1 | 7/2017 |
| WO | WO 2017/192785 A1 | 11/2017 |
| WO | WO 2017/192786 A1 | 11/2017 |
| WO | WO 2018/089497 A1 | 5/2018 |

OTHER PUBLICATIONS

Extended European Search Report for EP App. No. 16822078.8 dated Jan. 30, 2019.
International Search Report and Written Opinion for PCT/US2016/041653 dated Oct. 4, 2016.
International Preliminary Report on Patentability (Chapter I) for PCT/US2016/041653 dated Jan. 18, 2018.
Extended European Search Report for EP App. No. 16737769.6 dated May 3, 2018.
International Search Report and Written Opinion for PCT/US2016/013113 dated Mar. 21, 2016.
International Preliminary Report on Patentability (Chapter I) for PCT/US2016/013113 dated Jul. 27, 2017.
Partial Supplementary European Search Report for EP App. No. 15859824.3 dated Jun. 11, 2018.
Extended European Search Report dated Sep. 11, 2018 for Application No. EP 15859824.3.
International Search Report and Written Opinion for PCT/US2015/060689 dated Feb. 1, 2016.
International Preliminary Report on Patentability (Chapter I) for PCT/US2015/060689 dated May 16, 2017.
Partial Supplementary European Search Report for EP App. No. 15855640.7 dated May 30, 2018.
Extended European Search Report dated Sep. 5, 2018 for Application No. EP 15855640.7.
International Search Report and Written Opinion for PCT/US2015/058489 dated Mar. 11, 2016.
International Preliminary Report on Patentability (Chapter I) for PCT/US2015/058489 dated May 2, 2017.
European Search Report for EP App. No. 14836593.5 dated Feb. 23, 2017.
International Search Report and Written Opinion for PCT/US2014/051343 dated Dec. 18, 2014.
International Preliminary Report on Patentability (Chapter I) for PCT/US2014/051343 dated Feb. 16, 2016.
European Search Report for EP App. No. 12841329.1 dated Apr. 30, 2015.
Extended European Search Report dated Nov. 21, 2019 for Application No. EP 19187758.8.
International Preliminary Report on Patentability (Chapter I) PCT/US2012/060646 dated Apr. 22, 2014.
International Search Report and Written Opinion for PCT/US2012/060646 dated Feb. 25, 2013.
International Search Report and Written Opinion for PCT/US2016/050288 dated Jan. 12, 2016.
International Search Report and Written Opinion for PCT/US2016/050287 dated Jan. 3, 2017.
International Search Report and Written Opinion for PCT/US2017/030933 dated Jul. 21, 2017.
International Search Report and Written Opinion for PCT/US2017/030932 dated Sep. 19, 2017.
[No Author Listed], SQZ Biotech and AskBio Announce Research Collaboration to Create Immune Tolerization Products for AAV Gene Therapies. AskBio. Press Release. Nov. 7, 2019. 3 pages.
[No Author Listed], SQZ Biotech Announces Pricing of Initial Public Offering. SQZ Biotech. Press Release. Oct. 29, 2020. 2 pages.
[No Author Listed], SQZ Biotech Closes $65 Million Series D Financing. SQZ Biotech. Press Release. May 18, 2020. 2 pages.
[No Author Listed], SQZ Biotechnologies Presents Preclinical Data for their SQZ Tolerizing Antigen Carrier Platform in Antigen-Specific Immune Tolerance (ASIT) Digital Summit Invited Talk. SQZ Biotech. Press Release. Jan. 27, 2021. 4 pages.
Adamo et al., Microfluidic Cell Deformation as a Robust, Vector-Free Method for Cystosolic Delivery of Macromolecules. 2012 AIChE Annual Meeting. Oct. 2012;8 pages.
Adamo, Andrea et al., "Microfluidics-Based Assessment of Cell Deformability," Analytical Chemistry (Aug. 7, 2012), vol. 84, No. 15, pp. 6438-6443.
Alberts et al., Chapter 11: Ion Channels and the Electrical Properties of Membranes. Molecular Biology of the Cell, $4^{th}$ Ed. New York: Garland Science. 2002. 20 pages.
ATCC Thawing, Propagating, and Cryopreserving Protocol, NCI-PBCF-HTB81 (DU 145), Prostate Carcinoma (ATCC.RTM. htb-81), Version 1.6, 2012, 23 pages.
Augustsson et al. "Microfluidic, Label-Free Enrichment of Prostate Cancer Cells in Blood Based on Acoustophoresis," Analytical Chemistry, Aug. 28, 2012 (Aug. 28, 2012), vol. 84, No. 18, pp. 7954-7962.
Azarikia et al., Stabilization of biopolymer microgels formed by electrostatic complexation: Influence of enzyme (laccase) cross-linking on pH, thermal, and mechanical stability. Food Res Int. Dec. 2015;78:18-26. doi: 10.1016/j.foodres.2015.11.013. Epub Nov. 21, 2015.
Banz, A. et al., "Tumor Growth Control Using Red Blood Cells as the Antigen Delivery System and Poly(I:C)," J Immunother 2012, 35(5), pp. 409-417.
BD Bioscience FITC-labeled anti-CD45 antibody, 2 pages.
BD Bioscience PE-labeled anti-EpCAM antibody, 2 pages.
Blagovic et al., 165 Activating antigen carriers generated with microfluidics cell squeezing drive effective anti-tumor responses. JITC. Dec. 2020;8:A98-9. doi: 10.1136/jitc-2020-SITC2020.0165.

(56) References Cited

OTHER PUBLICATIONS

Boohaker et al. The Use of Therapeutic Peptides to Target and to Kill Cancer Cells. Curr Med Chem. (2012); 19(22), 26 page reprint.
Bosilkovski, This MIT PhD Just Raised $65 Million for His Clinical Stage Cell Therapy Company. Forbes. May 21, 2020. https://www.forbes.com/sites/igorbosilkovski/2020/05/21/meet-the-mit-phd-who-just-raised-65-million-for-his-clinical-stage-cell-therapy-company/?sh=1e9a48af9809 [last accessed Jan. 28, 2021]. 3 pages.
Cancer Facts & Figures 2012. Published by the American Cancer Society in Atlanta, 68 pages.
Chaw et al. Multi-step microfluidic device for studying cancer metastasis. Lab on a Chip (2007), v7, p. 1041-1047.
Chen et al., Patch clamping on plane glass-fabrication of hourglass aperture and high-yield ion channel recording. Lab Chip. Aug. 21, 2009;9(16):2370-80. Epub May 14, 2009. https://doi.org/10.1039/b901025d.
Cremel, L. et al., "Innovative approach in Pompe disease therapy: Induction of immune tolerance by antigen-encapsulated red blood cells," Int J Pharm. Aug. 1, 2015;491(1-2), pp. 69-77.
Cremel, L. et al., "Red blood cells as innovative antigen carrier to induce specific immune tolerance," Int J Pharm. Feb. 25, 2013;443(1-2), pp. 39-49.
Cross et al., "Nanomechanical analysis of cells from cancer patients," Nature Nanotechnology (Dec. 2007), vol. 2, pp. 780-783.
Ding, X. et al., "High-throughput nuclear delivery and rapid expression of DNA via mechanical and electrical cell-membrane disruption," Nature Biomedical Engineering (2017), vol. 1, No. 3, 7 pages.
Ditommaso et al., Cell engineering with microfluidic squeezing preserves functionality of primary immune cells in vivo. PNAS. Oct. 2018;115(46):E10907-14.
Downs, C. A. et al. (May 14, 2011). "Cell Culture Models Using Rat Primary Alveolar type 1 Cells", Pulmonary Pharm. & Therapeutics 24(5)577-586.
Eixarch, H. et al. "Tolerance induction in experimental autoimmune encephalomyelitis using non-myeloablative hematopoietic gene therapy with autoantigen." Molecular Therapy 17.5 (2009): 897-905.
Escoffre et al., What is (still not) known of the mechanism by which electroporation mediates gene transfer and expression in cells and tissues. Mol Biotechnol. Mar. 2009;41(3):286-95. doi: 10.1007/s12033-008-9121-0. Epub Nov. 18, 2008.
Esposito et al., "Intraerythrocytic administration of a synthetic Plasmodium antigen elicits antibody response in mice, without carrier molecules or adjuvants," International Journal of Parasitology, vol. 20, No. 8, pp. 1109-1111 (1990).
Fagerlund et al., The Cpf1 CRISPR-Cas protein expands genome-editing tools. Genome Biol. Nov. 17, 2015;16:251. doi: 10.1186/s13059-015-0824-9.
Favretto, M. E. et al., "Human erythrocytes as drug carriers: Loading efficiency and side effects of hypotonic dialysis, chlorpromazine treatment and fusion with liposomes," Journal of Controlled Release 2013; 170: 343-351.
Gasteiger et al. The Proteomics Handbook (2005), Chapter 52, pp. 571-607.
Gilbert, T-cell-inducing vaccines—what's the future. Immunology. Jan. 2012;135(1):19-26. doi: 10.1111/j.1365-2567.2011.03517.x.
Golzio et al., Direct visualization at the single-cell level of electrically mediated gene delivery. Proc Natl Acad Sci U S A. Feb. 5, 2002;99(3):1292-7. doi: 10.1073/pnas.022646499. Epub Jan. 29, 2002.
Gossett et al., Hydrodynamic stretching of single cells for large population mechanical phenotyping. PNAS. May 2012;109(20):7630-5.
Griesbeck et al., "Sex Differences in Plasmacytoid Dendritic Cell Levels of IRF5 Drive higher IFN-alpha production in Women," The Journal of Immunology (Dec. 2015), vol. 195(11):5327-5336.
Grimm, A. J. et al., "Memory of tolerance and induction of regulatory T cells by erythrocyte-targeted antigens," Sci Rep. Oct. 29, 2015;5:15907, 11 pages.
Hallow et al., "Shear-Induced Intracellular Loading of Cells With Molecules by Controlled Microfluidics," Biotechnology and Bioengineering (2008), vol. 99(4):846-854.
Han, X. et al., "CRISPR-Cas9 delivery to hard-to-transfect cells via membrane deformation," Sci. Adv., Aug. 14, 2015, e1500454, 8 pp.
Hillerdal et al., "Systemic treatment with CAR-engineered T cells against PSCA delays subcutaneous tumor growth and prolongs survival of mice," BMC Cancer (Jan. 18, 2014), vol. 14, No. 30, pp. 1-9.
Hoeppener A.E.L.M., Swennenhuis J.F., Terstappen L.W.M.M. (2012) Immunomagnetic Separation Technologies. In: Ignatiadis M., Sotiriou C., Pantel K. (eds) Minimal Residual Disease and Circulating Tumor Cells in Breast Cancer. Recent Results in CancerResearch, vol. 195. Springer, Berlin, Heidelberg.
Hoskin et al. Studies on anticancer activities of antimicrobial peptides. Biochimica et Biophyscia Acta (2008), v1778, p. 357-375.
Hosokawa et al. Size-Selective Microcavity Array for Rapid and Efficient Detection of Circulating Tumor Cells. Anal. Chem. (2010), v82, p. 6629-6635.
Howarth, M. et al. (May 2008). "Monovalent, Reduced-Size Quantum Dots for Imaging Receptors on Living Cells," Nature Methods 5(5):397-399.
Janeway Jr et al. Immunobiology: The Immune System in Health and Disease. 5th edition (2001), Chapter "The structure of a typical antibody molecule", NCBI Bookshelf NBK27144, 5 page reprint.
Jiang, The immunopotentiators and delivery systems for use in vaccines. Prog Microbiol Immunol. Dec. 31, 2012;(3):1-8.
Kiani et al., Cas9 gRNA engineering for genome editing, activation and repression. Nature Methods. 2015;12:1051-4.
Kim, D., et al., "Microengineered Platforms for Cell Mechanobiology," Annual Review of Biomedical Engineering, 2009, vol. 11, pp. 203-233.
Lee et al., "Nonendocytic delivery of functional engineered nanoparticles into the cytoplasm of live cells using a novel, high-throughput microfluidic device," Nano Letters (2012), vol. 12, pp. 6322-6327.
Li, J. et al., "Microfluidic-Enabled Intracellular Delivery of Membrane Impermeable Inhibitors to Study Target Engagement in Human Primary Cells," ACS Chemical Biology 2017, vol. 12, No. 12, pp. 2970-2974.
Lin et al., "Highly selective biomechanical separation of cancer cells from leukocytes using microfluidic and hydrodynamic concentrator," Biomicrofluidics (Jun. 26, 2013), vol. 7, No. 3, pp. 34114-1-11.
Liu et al., "Molecular imaging in tracking tumor-specific cytotoxic T lymphocytes (CTLs)," Theranostics (Jul. 28, 2014), vol. 4, No. 10, pp. 990-1001.
Liu et al., "Spatially selective reagent delivery into cancer cells using a two-layer microfluidic culture system," Analytica Chimica Acta (Sep. 1, 2012), vol. 743, pp. 125-130.
Liu, W. et al. (Jan. 20, 2010). "Compact Biocompatible Quantum Dots Via RAFT-Mediated Synthesis of Imidazole-Based Random Copolymer Ligand," JACS 132(2):472-483.
Lorentz, K. M. et al., "Engineered binding to erythrocytes induces immunological tolerance to E. coli asparaginase," Sci Adv. Jul. 17, 2015;1(6):e1500112, 11 pages.
Mali, P. et al., "RNA-guided human Genome Engineering via Cas9," Science (2013), vol. 339, No. 6121, pp. 823-826.
Maratou et al., Glucose transporter expression on the plasma membrane of resting and activated while blood cells. European Journal of Clinical Investigation. 2007;37:282-90.
Matthews, B.D., et al., "Cellular adaptation to mechanical stress: role of integrins, Rho, cytoskeletal tension and mechanosensitive ion channels," Journal of Cell Science, vol. 119, pp. 508-518, 2006.
Milo, R. "What is the total number of protein molecules per cell volume? A call to rethink some published values." Bioessays 35.12 (2013): 1050-1055.
Murphy, J. S. et al. (Sep. 1, 1956, e-pub May 2004). "Measurement of Wall Shearing Stress in the Boundary Layer by Means of an Evaporating Liquid Film," Journal of Applied Physics 27(9):1097-1103.
Nic An Tsaoir et al., Scalable Antibody Production from CHO Cell Line of Choice Using Flow Electroporation. MaxCyte. Jun. 2016. 1 page.

(56) References Cited

OTHER PUBLICATIONS

Novokhatskiy et al., Problema kontaminatsii kletkami I novyie podkhody k kontroliu perevivaiemykh liniy. Voprosy virusologii. 1977;4:396-408.

Ogurtsov et al., Biotechnology. Principles and Application Training Manual. Ministry of Education and Science. 2012. 344 pages.

Paganin-Gioanni et al., Direct visualization at the single-cell level of siRNA electrotransfer into cancer cells. Proc Natl Acad Sci U S A. Jun. 28, 2011;108(26):10443-7. doi: 10.1073/pnas.1103519108. Epub Jun. 13, 2011.

Polvani et al., "Murine Red Blood Cells as Efficient Carriers of Three Bacterial Antigens for the Production of Specific and Neutralizing Antibodies," Biotechnology and Applied Biochemistry, vol. 14, pp. 347-356 (1991).

Ramakrishnan et al., 1743-P: Engineering Erythrocytes with the SQZ Cell Therapy Platform to Enhance Immunotolerance. Diabetes. Jun. 2019;68(Supplement 1). https://doi.org/10.2337/db19-1743-P. Abstract.

Ravilla et al., "Erythrocytes as Carrier for Drugs, Enzymes and Peptides," Journal of Applied Pharmaceutical Science, vol. 2, No. 2, pp. 166-176 (2012).

Rossi, L. et al., "Erythrocyte-mediated delivery of phenylalanine ammonia lyase for the treatment of phenylketonuria in BTBR-Pah. sup.enu2 mice," Journal of Controlled Release 194; 37-44 (2014).

Rughetti, A. et al., "Transfected human dendritic cells to induce antitumor immunity," Gene Therapy, vol. 7, pp. 1458-1466 (2000).

Rutella et al., "Tolerogenic dendritic cells: cytokine modulation comes of age," Blood, vol. 108, No. 5, pp. 1435-1440 (2006).

Sharei et al, "Ex vivo Cytosolic Delivery of Functional Macromolecules to Immune Cells," (Apr. 13, 2015), PLOS One, vol. 10, No. 4, 12 pp. e0118803.

Sharei et al., "A vector-free microfluidic platform for intracellular delivery," Proc. Natl. Acad. Sci. USA (Feb. 5, 2013), vol. 110, No. 6, pp. 2082-2087.

Sharei et al., "A vector-free microfluidic platform for intracellular delivery," Proc. Natl. Acad. Sci. USA (Feb. 5, 2013), vol. 110, No. 6, Supporting Information. 10 pages.

Sharei et al., "Cell Squeezing as a Robust, Microfluidic Intracellular Delivery Platform," Journal of Visualized Experiments (Nov. 7, 2013), No. 81, 9 pp.

Sharei et al., "Plasma membrane recovery kinetics of a microfluidic intracellular delivery platform," Integrative Biology (2014), vol. 6, pp. 470-475.

Shelby et al., "A microfluidic model for single-cell capillary obstruction by Plasmodium falciparum infected erythrocytes," (Dec. 9, 2003), Proc. Nat. Acad. Sci., vol. 100, No. 25, pp. 14618-14622.

Song et al., Scientific basis for the use of hypotonic solutions with ultrasonic liposuction. Aesthetic Plast Surg. Mar.-Apr. 2006;30(2):233-8. doi: 10.1007/s00266-005-0087-z.

Steinman et al., "Tolerogenic dendritic cells," Annual Review of Immunology, vol. 21, pp. 685-711 (2003).

Stevenson, D. J. et al., "Single cell optical transfection," IEEE Transactions on Ultrasonics, Ferroelectrics and Frequency Control, vol. 53, No. 1, 863-871 (2010).

Stevenson, D. J. et al., "Single cell optical transfection," J. R. Soc. Interface, vol. 7, 863-871 (2010).

Stewart et al., "In vitro and ex vivo strategies for intracellular delivery," Nature, vol. 538, No. 7624, pp. 183-192 (2016).

Swaminathan et al. Mechanical Stiffness Grades Metastatic Potential in Patient Tumor Cells and in Cancer Cell Lines. Cancer Research (2011) , v71(15), p. 5075-5080.

Szeto et al., "Microfluidic squeezing for intracellular antigen loading in polyclonal B-cells as cellular vaccines," Scientific Reports, vol. 5, 10276 (May 2015), 13 pages.

Tlaxca, J. L. et al., "Analysis of in vitro Transfection by Sonoporation Using Cationic and Neutral Microbubbles," Ultrasound in Medicine and Biology, vol. 36, No. 11, 1907-1918 (2010).

Tran et al., Expansion of immature, nucleated red blood cells by transient low-dose methotrexate immune tolerance induction in mice. Clin Exp Immunol. Nov. 18, 2020;0:1-15. doi: 10.1111/cei. 13552.

Vechkanov et al., Osnovy kletochnoy inzhenerii: Study guide. Rostov-on-Don. 2012; 133 pages. Relevant pp. 15-16.

Vinulan, SQZ Biotech Lines Up an IPO on the NYSE to Fund Cell Therapy R&D. Xconomy. Oct. 12, 2020. https://xconomy.com/boston/2020/10/12/sqz-biotech-lines-up-an-ipo-on-the-nyse-to-fund-cell-therapy-rd/ [last accessed Jan. 28, 2021]. 3 pages.

Weaver et al., A brief overview of electroporation pulse strength-duration space: A region where additional intracellular effects are expected. Bioelectrochemistry. Oct. 2012;87:236-43.

Wen et al., Shear Effects on Stability of DNA Complexes in the Presence of Serum. Biomacromolecules. Oct. 9, 2017;18(10):3252-3259. doi: 10.1021/acs.biomac.7b00900. Epub Sep. 1, 2017.

Williams, A.R. et al. (Nov. 5, 1999). "Filtroporation: A Simple, Reliable Technique for Transfection and Macromolecular Loading of Cells", Biotechnology and Bioengineering 65(3)341-346.

Wright et al., Rational design of a split-Cas9 enzyme complex. PNAS. Mar. 2015;112(10):2984-9.

Yangulov et al., Vliyaniye razlichnykh kriozashchitnykh sred na zhiznesposobnost kriokonservirovannykh limfoblastnykh kletochnyk liniy H-9 I U-937. Problemy kriobiologii. 1991;3:46-9.

Ye, Complexation between milk proteins and polysaccharides via electrostatic interaction: principles and applications—a review. Int J Food Sci Technol. Jan. 31, 2008;43(3):406-15.

Yin et al., "Delivery technologies for genome editing," Nature Reviews (2017), vol. 16, No. 6, pp. 387-399.

Zarnitsyn et al., "Electrosonic ejector microarray for drug and gene delivery," Biomed Microdevices (2008) 10:299-308.

Zdobnova et al., Self-Assembling Complexes of Quantum Dots and scFv Antibodies for Cancer Cell Targeting and Imaging. PLOS One. 2012;7(10):e48248. 8 pages.

Zhdanov et al., Tayna tretiego tsarstva. Znaniye. 1975; 176 pages. Relevant pp. 124-125.

U.S. Appl. No. 15/865,901, filed Jan. 9, 2018, Sharei et al.
U.S. Appl. No. 15/542,892, filed Nov. 27, 2017, Sharei et al.
U.S. Appl. No. 15/523,142, filed Apr. 28, 2017, Sharei et al.
U.S. Appl. No. 16/145,865, filed Sep. 28, 2018, Sharei et al.
U.S. Appl. No. 16/141,107, filed Sep. 25, 2018, Sharei et al.
U.S. Appl. No. 16/818,021, filed Mar. 13, 2020, Sharei et al.
EP 16822078.8, Jan. 30, 2019, Extended European Search Report.
PCT/US2016/041653, Oct. 4, 2016, International Search Report and Written Opinion.
PCT/US2016/041653, Jan. 18, 2018, International Preliminary Report on Patentability (Chapter 1).
EP 16737769.6, May 3, 2018, Extended European Search Report.
PCT/US2016/013113, Mar. 21, 2016, International Search Report and Written Opinion.
PCT/US2016/013113, Jul. 27, 2017, International Preliminary Report on Patenability (Chapter 1).
EP 15859824.3, Jun. 11, 2018, Partial Supplementary European Search Report.
EP 15859824.3, Sep. 11, 2018, Extended European Search Report.
PCT/US2015/060689, Feb. 1, 2016, International Search Report and Written Opinion.
PCT/US2015/060689, May 16, 2017, International Preliminary Report on Patentability (Chapter 1).
EP 15855640.7, May 30, 2018, Partial Supplementary European Search Report.
EP 15855640.7, Sep. 5, 2018, Extended European Search Report.
PCT/US2015/058489, Mar. 11, 2016, International Search Report and Written Opinion.
PCT/US2015/058489, May 2, 2017, International Preliminary Report on Patentability (Chapter 1).
EP 14836593.5, Feb. 23, 2017, European Search Report.
PCT/US2014/051343, Dec. 18, 2014, International Search Report and Written Opinion.
PCT/US2014/051343, Feb. 16, 2016, International Preliminary Report on Patentability (Chapter 1).
EP 12841329.1, Apr. 30, 2015, European Search Report.
EP 19187758.8, Nov. 21, 2019, Extended European Search Report.

(56) References Cited

OTHER PUBLICATIONS

PCT/US2012/060646, Apr. 22, 2014, International Preliminary Report on Patentability (Chapter 1).
PCT/US2012/060646, Feb. 25, 2013, International Search Report and Written Opinion.
PCT/US2016/050288, Jan. 12, 2016, International Search Report and Written Opinion.
PCT/US2016/050287, Jan. 3, 2017, International Search Report and Written Opinion.
PCT/US2017/030933, Jul. 21, 2017, International Search Report and Written Opinion.
PCT/US2017/030932, Sep. 19, 2017, International Search Report and Written Opinion.
Extended European Search Report for EP Application No. 21158382.8 dated Jun. 11, 2021.
Baumann et al., Hemolysis of human erythrocytes with saponin affects the membrane structure. Acta Histochem. Feb. 2000;102(1):21-35. doi: 10.1078/0065-1281-00534.
Berrington et al., Lymphocyte subsets in term and significantly preterm UK infants in the first year of life analysed by single platform flow cytometry. Clin Exp Immunol. May 2005;140(2):289-92. doi: 10.1111/j.1365-2249.2005.02767.x.
Carlson et al., Self-Sorting of White Blood Cells in a Lattice. PRL. Sep. 15, 1997;79(11):2149-52.
De Clercq et al., Antiviral agents active against human herpesviruses HHV-6, HHV-7 and HHV-8. Rev Med Virol. Nov.-Dec. 2001;11(6):381-95. doi: 10.1002/rmv.336.
De Clercq, Antiviral drugs in current clinical use. J Clin Virol. Jun. 2004;30(2):115-33. doi: 10.1016/j.jcv.2004.02.009.
Getasew et al., Advanced malaria treatment in pregnant women. Eur J Clin Pharm. Sep.-Oct. 2017;19(5):325-34.
Hoffman, On Red Blood Cells, Hemolysis and Resealed Ghosts. In: The Use of Resealed Erythrocytes as Carriers and Bioreactors. 1992. Magnani et al.,. Eds. Chapter 1:1-15.
Hori et al., Control of regulatory T cell development by the transcription factor Foxp3. Science. Feb. 14, 2003;299(5609):1057-61. doi: 10.1126/science.1079490. Epub Jan. 9, 2003.
Johnson et al., Loss of resealing ability in erythrocyte membranes. Effect of divalent cations and spectrin release. Biochim Biophys Acta. May 4, 1978;509(1):58-66. doi: 10.1016/0005-2736(78)90007-X. Abstract only.
Kinosita Jr. et al., Survival of sucrose-loaded erythrocytes in the circulation. Nature. Mar. 16, 1978;272(5650):258-60. doi: 10.1038/272258a0.
Lee et al., Kinetic studies of human erythrocyte membrane resealing. Biochim Biophys Acta. Apr. 26, 1985;815(1):128-34. doi: 10.1016/0005-2736(85)90482-1. Abstract only.
Lizano et al., Mouse erythrocytes as carriers for coencapsulated alcohol and aldehyde dehydrogenase obtained by electroporation in vivo survival rate in circulation, organ distribution and ethanol degradation. Life Sci. Mar. 16, 2001;68(17):2001-16. doi: 10.1016/s0024-3205(01)00991-2.
Loschko et al., Antigen targeting to plasmacytoid dendritic cells via Siglec-H inhibits Th cell-dependent autoimmunity. J Immunol. Dec. 15, 2011;187(12):6346-56. doi: 10.4049/jimmunol.1102307. Epub Nov. 11, 2011.
Magnani et al., Erythrocyte engineering for drug delivery and targeting. Biotechnol Appl Biochem. Aug. 1998;28(1):1-6.
McNeil et al., Coping with the inevitable: how cells repair a torn surface membrane. Nat Cell Biol. May 2001;3(5):E124-9. doi: 10.1038/35074652. Abstract only.
McNeil et al., Plasma membrane disruption: repair, prevention, adaptation. Annu Rev Cell Dev Biol. 2003;19:697-731. doi: 10.1146/annurev.cellbio.19.111301.140101.
McNeil et al., The endomembrane requirement for cell surface repair. Proc Natl Acad Sci U S A. Apr. 15, 2003;100(8):4592-7. doi: 10.1073/pnas.0736739100. Epub Apr. 2, 2003.
McNeil, Repairing a torn cell surface: make way, lysosomes to the rescue. J Cell Sci. Mar. 1, 2002;115(Pt 5):873-9.
Nagel et al., HbS-oman heterozygote: a new dominant sickle syndrome. Blood. Dec. 1, 1998;92(11):4375-82.
Patel et al., Drug loaded erythrocytes: as novel drug delivery system. Curr Pharm Des. 2008;14(1):63-70. doi: 10.2174/138161208783330772.
Razizadeh et al., Coarse-Grained Modeling of Pore Dynamics on the Red Blood Cell Membrane under Large Deformations. Biophys J. Aug. 4, 2020;119(3):471-482. doi: 10.1016/j.bpj.2020.06.016. Epub Jun. 24, 2020.
Reddy et al., Plasma membrane repair is mediated by Ca(2+)-regulated exocytosis of lysosomes. Cell. Jul. 27, 2001;106(2):157-69. doi: 10.1016/s0092-8674(01)00421-4.
Redman, Phospholipid metabolism in intact and modified erythrocyte membranes. J Cell Biol. Apr. 1971;49(1):35-49. doi: 10.1083/jcb.49.1.35.
Ring et al., Targeting of autoantigens to DEC205$^+$ dendritic cells in vivo suppresses experimental allergic encephalomyelitis in mice. J Immunol. Sep. 15, 2013;191(6):2938-47. doi: 10.4049/jimmunol.1202592. Epub Aug. 14, 2013.
Sachs, Potassium-potassium exchange as part of the over-all reaction mechanism of the sodium pump of the human red blood cell. J Physiol. May 1986;374:221-44. doi: 10.1113/jphysiol.1986.sp016076.
Salgado et al., Red blood cell membrane-facilitated release of nitrite-derived nitric oxide bioactivity. Biochemistry. Nov. 10, 2015;54(44):6712-23. doi: 10.1021/acs.biochem.5b00643. Epub Oct. 28, 2015. Abstract only.
Saulis, The loading of human erythrocytes with small molecules by electroporation. Cell Mol Biol Lett. 2005;10(1):23-35.
Schatzmann et al., Calcium movements across the membrane of human red cells. J Physiol. Apr. 1969;201(2):369-95. doi: 10.1113/jphysiol.1969.sp008761.
Tsai et al., Reversal of autoimmunity by boosting memory-like autoregulatory T cells. Immunity. Apr. 23, 2010;32(4):568-80. doi: 10.1016/j.immuni.2010.03.015. Epub Apr. 8, 2010.
U.S. Appl. No. 17/689,745, filed Mar. 8, 2022, Sharei et al.
U.S. Appl. No. 17/404,286, filed Aug. 17, 2021, Sharei et al.
U.S. Appl. No. 17/394,125, filed Aug. 4, 2021, Sharei et al.
U.S. Appl. No. 17/509,229, filed Oct. 25, 2021, Sharei et al.
EP 21158382.8, Jun. 11, 2021, Extended European Search Report.

* cited by examiner

Protocol

1. Lyse red blood cells

2. Deliver dye via CellSqueeze

3. Sort cells

Fluorescent Label + & CD45 -          Fluorescent Label - or CD45 +

SELECTIVE DELIVERY OF MATERIAL TO CELLS

CROSS-REFERENCE TO RELATED APPLICATION

This application is a continuation of U.S. application Ser. No. 16/145,865, filed Sep. 28, 2018, entitled "SELECTIVE DELIVERY OF MATERIAL TO CELLS", which is a continuation of U.S. application Ser. No. 14/912,001, filed Feb. 12, 2016, entitled "SELECTIVE DELIVERY OF MATERIAL TO CELLS", which is a national stage filing under 35 U.S.C. § 371 of International patent Application Serial No. PCT/US2014/051343, filed Aug. 15, 2014, which claims priority to U.S. Provisional patent Application No. 61/866,972 filed Aug. 16, 2013, the entire contents of which is hereby expressly incorporated by reference.

GOVERNMENT SUPPORT

This invention was made with Government support under Grant Nos. R01 GM101420, P30 CA014051, and EB011187 awarded by the National Institutes of Health. The Government has certain rights in the invention.

TECHNICAL FIELD

The field of the invention relates to size-selective delivery of material to cells.

BACKGROUND

Intracellular delivery of materials is a challenge. Existing technologies that rely on nanoparticles, electrical fields, pore-forming chemicals, etc. are capable of delivering some materials to certain cell types but often in an indiscriminant fashion with regards to the physical properties of the target cell. By developing selective delivery methods dependent on the physical properties of the target cells, one could exert more robust control in delivery activity for research, diagnostic or therapeutic applications. For example, Circulating tumor cells (CTCs) are tumor cells found in the bloodstream, believed to mediate metastasis, or the spread of cancer, to distant sites in the body. Approximately 90% of human deaths from cancer are due to metastasis. Identification and characterization of CTCs could be the key to understanding, treating, or preventing metastatic cancer. Moreover these cells are known to have different physical properties compared to the surrounding blood cells.

SUMMARY

The current subject matter provides devices, systems, and methods for selectively delivering material to one or more cells based on their physical properties, such as size, volume, diameter, cytosol viscosity, or membrane stiffness. For example materials can be delivered in a cell size dependent manner. A cell suspension containing differentially sized cells can be run through a device in the presence of the target delivery material (e.g., a dye, a protein, nucleic acid, and the like) and these materials can be selectively delivered to the larger cells within the population. The mechanism of delivery in the data being through selective disruption of the cell membrane of larger cells as they are deformed in a channel constriction while smaller cells are not deformed enough to cause membrane disruption.

In some example implementations, labelling tumor cells relative to non-tumor cells can be achieved. Cells are run through a device for size selective tagging using fluorescent dyes or other detectable markers. The cells are optionally stained with an antibody, e.g., a tumor cell selective antibody, e.g., antibodies against CD45 to provide further contrast between cancer cells and blood cells (most blood cells are CD45+). The samples are run through a cell sorter, e.g. a standard fluorescence-activated cell sorter (FACS).

In some example implementations, labeling of cells based on their cell cycle can be achieved because cells within a population that are closer to division are larger than those that have just undergone division. Delivery of a dye to the bigger cells within a population can be used to identify the individual cells that are in a later stage of their cell cycle.

In some example implementations, therapeutics for blood cancers (e.g. lymphomas) can be achieved because lymphoma cells are often bigger than the surrounding blood cells thus an intracellular toxin can be delivered to lymphoma cells but not the healthy surrounding blood cells. This can induce selective death of diseased cells.

Tagged cells can be isolated by fluorescence or magnetic purification techniques. Flow cytometry or microarrays with robotic manipulators can be used to select cells based on fluorescence, while magnetic columns, microfluidic magnetic separation systems, or magnetic sweepers can be used to isolate magnetically tagged particles.

Cells can be identified based on relative size or diameter. Thus, relatively larger cells selectively or preferentially take up markers, because the extent of cell membrane disruption is relatively greater in larger cells, i.e., larger cells are deformed to a greater extent compared to smaller cells. Due to the greater degree of membrane disruption of larger cells, at least 10%, 25%, 50%, 2-fold, 5-fold, 10-fold, 100-fold or more of a payload molecule gains access to the inside (cytoplasm) of a larger cell compared to a smaller cell. As a result of the uptake of detectable markers in this manner and subsequent sorting based on uptake of the marker, the purity of tumor cells is enhanced by 100 times; 1,000 times, and up to 10,000 times or more compared to the level of purity in peripheral blood. Purity is assessed by an antibody that targets/binds to a known marker that is expressed/overexpressed by tumor cells. Alternatively, antibodies against markers that are not expressed by tumor cells but are expressed/overexpressed by blood cells (CD45 is an example). Either approach helps provide increased contrast to sort out the cells of interest.

Samples with high size-tag fluorescence and low CD45 fluorescence are captured as candidate/potential CTCs. FACS outputs are inherently relative. A "high" signal is minimum one decade (ten times higher level) of fluorescence intensity above the baseline control signal, and a "low" is one decade below the positive control population.

The device and methods of the invention provide a solution to the long-standing problem of how to identify and/or isolate approximately for more (2, 5, 10, 100, 1,000 or more) CTCs per 1-10 million leukocytes in a patient-derived sample of blood. For example, 1 CTC per ml of blood is clinically relevant in a cancer patient. Accordingly, a method for isolating or identifying a circulating tumor cell comprises the steps of providing a cell suspension; passing the solution through a microfluidic channel that includes a constriction, the constriction being sized to preferentially deform a circulating tumor cell compared to a leukocyte; passing the cell suspension through the constriction; and contacting the cell suspension solution with a detectable marker. The suspension can be passed through a microfluidic channel that includes a constriction, the constriction being sized to preferentially deliver a compound to a group of cells having a relatively different physical property than another group of cells. The physical property can include cell size, diameter, cytosol viscosity, and/or membrane stiffness (e.g., as measured by transit time assays, stiffer cells pass through specialized microchannels more slowly than less stiff cells, e.g., as described in Sharei et al., 2012, Anal. Chem. 84(15):6438-6443; Cross et al., 2007, Nature Nanotechnology 2:780-783). The contact can happen after deformation treatment. Or the material can be premixed with the cells before deformation treatment. Both CTCs and leukocytes are deformed; however larger cells are deformed to a greater degree and therefore, molecules are selectively delivered to such cells, thereby treating or tagging them.

For example, the marker comprises a detectably labeled, e.g., fluorescently or magnetically labeled material, such as a dye or particle. The dyes or particles need not be tumor specific. Optionally, they differentially bind to tumor cells (e.g., at least 20%, 50%, 2 times, 5 times, or more compared to non-tumor cells). However, the specificity of the method is based on the discovery that tumor cells are slightly larger than leukocytes and the device is highly size selective. This size difference depends on the tumor type. For example, tumor cells are generally from 50%-400% larger than the leukocytes. Therefore, the delivery material preferentially enters into cells that are large enough to be tagged via size-specific deformation of cells. The delivered tag is then in turn detected to identify the CTC.

In one example, the suspension comprises whole blood. Alternatively, the cell suspension is a mixture of cells in a physiological saline solution other than blood. Typically, the cell suspension comprises whole blood of a subject at risk of or diagnosed as comprising a tumor. For example, the patient is suspected of having, has been diagnosed as having, or is suspected or diagnosed as having metastatic disease of melanoma, colon, prostate, breast, liver, lung, pancreatic, brain, or blood. CTCs can be present before the patient has developed metastatic disease. Therefore, early detection of CTCs is clinically important, because such detection represents an early identification of patients likely to progress to develop metastatic disease.

Optionally, erythrocyte lysis is carried out as a pretreatment step prior to flowing cells through the device.

The device is characterized by physical parameters that distinguish tumor cells from non-tumor cells, e.g., normal erythrocytes or leukocytes. For example, the constriction comprises a width from 4 μm-10 μm, length of 1 μm-100 μm, and 1-10 constrictions in series. The estimated speed of the cells can range from 10 mm/s to 10 m/s. To push or propel the cell suspension through the device, the method further comprises applying a pressure to cells. Pressure is used to drive the cell suspension through the device, and the transit through the constriction point is what deforms the cells and leads to membrane disruption, and therefore delivery.

The method involves introducing into the tumor cell a detectable compound. Thus, the cell suspension comprises a payload or the method further comprises a step of incubating said cell suspension in the solution containing a payload for a predetermined time after it passes through the constriction. For example, the payload comprises a magnetic particle such as a nanoparticle, a fluorescent particle, such as a quantum dot or carbon nanotube, or a fluorescent dye or protein, or genetic material (DNA or RNA) that codes for a fluorescent protein or other compound that enables detection (e.g., luciferase). Alternatively one could deliver a combination of the aforementioned materials to enable detection and simultaneous manipulation of the cells. For example, one could deliver a fluorescent particle to enable sorting and co-deliver DNA, RNA or a protein to facilitate subsequent tumor cell survival and encourage its growth and proliferation post-sorting to enable further studies of cultured metastatic cells.

Also within the invention is a microfluidic system for distinguishing tumor cells from non-tumor cells, comprising a microfluidic channel defining a lumen and being configured such that a tumor cell suspended in a buffer can pass therethrough and is constricted compared to a non-tumor cell. Non tumor cells may be deformed to some extent; however, the key is that the tumor cells are deformed enough to cause a cell membrane disruption whereas the non-tumor cells are not deformed enough to result in membrane disruption due to their smaller relative size. The membranes of smaller cells are not disrupted or disrupted less than larger cells, e.g., in some cases, both smaller and larger cells are disrupted but smaller cells receive less material than the larger cells. The microfluidic channel includes a cell-deforming constriction, wherein a diameter of the constriction is a function of the diameter of the cell. The constriction is sized to preferentially deform a tumor cell compared to a non-tumor cell. This preferential deformation is designed to selectively facilitate the delivery of the target material to tumor cells vs. non tumor cells. Selective delivery enables one to enrich the desired tumor population through sorting/enrichment methods such as flow cytometery (FACS), micromanipulation, magnetic separation, cell culture.

The method is carried out at physiological temperature, e.g., 37° C., room temperature, e.g., 20° C., or alternatively, at 0-4° C. In some cases, the latter is preferred, because it can yield better delivery performance due to delayed membrane repair and minimize background from endocytosis by reducing the endocytotic activity of cells. As described above, the cell suspension is whole blood or any mammalian cell suspension in a physiological buffer solution such as phosphate buffers saline (PBS) or tissue culture media as a delivery buffer. In some examples, PBS is preferred due to reduced effects from Ca or Mg in tissue culture media.

In an aspect, isolating or identifying a cell based on a physical property of the cell can include providing a cell suspension; passing the suspension through a microfluidic channel that includes a constriction; passing the cell suspension through the constriction; and, contacting the cell suspension solution with a compound. The constriction can be sized to preferentially deform a relatively larger cell compared to a relatively smaller cell.

In another aspect, a microfluidic system for distinguishing tumor cells from non-tumor cells can include a microfluidic channel defining a lumen and being configured such that a tumor cell suspended in a buffer can pass therethrough and is constricted compared to a non-tumor cell. The microfluidic channel can include a cell-deforming constriction. A diameter of the constriction can be a function of the diameter of the cell.

One or more of the following features can be included. For example, the physical property can be one or more of size and diameter. The cell suspension can include one or more of: peripheral blood cells; and at least two different cell types having different physical properties. The cell suspension can include an erythrocyte-depleted population of peripheral blood cells. The larger cell can include a circulating tumor cell and the smaller cell can include a leukocyte. The compound can include a molecular mass of 0.5 kDa to 5 MDa. The compound can include a molecular mass of 3 kDa to 10 kDa. The compound can include a detectable marker (e.g., quantum dots, cyanine, fluorescein, rhodamine, and derivatives thereof such as fluorescein isothiocyanate (FITC) or Tetramethylrhodamine isothiocyanate (TRITC) or NHS-Rhodamine, maleimide activated fluorophores such as fluorescein-5-maleimide, as well as Alexa Fluors), an active biomolecule, and/or a toxin, (e.g., *Pseudomonas* exotoxin, Diphtheria toxin, and ricin, caspase proteins, antibodies that interfere with essential cell functions (e.g. antibodies against tubulin)) for selectively killing target cells. The compound can influence cell function (e.g. transcription factors, siRNA, DNA, mRNA, antibodies, small molecule drugs) and/or can induce cell death. The compound can enter the cell after the cell has passed through the constriction. The suspension can include whole blood. The suspension can include whole blood of a subject at risk of or diagnosed as comprising a tumor. The tumor can include melanoma, colon, prostate, lung, pancreatic, breast, liver, brain, or blood cancer. The constriction can include a width from 4 μm-10 μm, length of 1 μm-100 μm, and 1-10 constrictions in series. A speed of the cells traversing a constriction can range from 10 mm/s to 10 m/s. A pressure can be applied to the cell suspension to drive cells through the constriction of a microfluidic channel.

The cell suspension can include a payload or the cell suspension can be incubated in the solution containing a payload for a predetermined time after it passes through the constriction. The payload can include a magnetic particle a fluorescent particle, such as a quantum dot or carbon nanotube, or a fluorescent dye or protein, or genetic material (DNA or RNA) that codes for a fluorescent protein or other compound that enables detection (e.g. luciferase). The constriction can be sized to preferentially deform a tumor cell more than a non-tumor cell.

These and other capabilities of the invention, along with the invention itself, will be more fully understood after a review of the following figures, detailed description, and claims.

DETAILED DESCRIPTION

CTCs are tumor cells that are found in the bloodstream, and are believed to be responsible for the dissemination of cancer to distant organs. CTCs are regarded as minimally-invasive, "liquid biopsies" for cancer patients and are useful as prognostic indicators for patient outcome and treatment efficacy. Comprehensive characterizations of these single cells provide a better understanding of metastatic dissemination, treatment resistance, and tumor biology.

Figure 1:
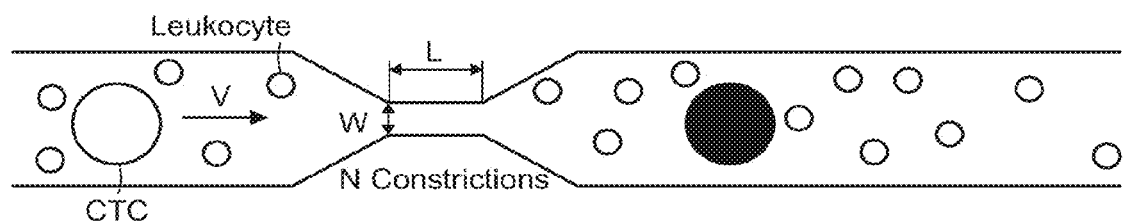
FIG. 1 is a diagram of a system for size selective tagging of CTCs by rapid mechanical deformation.

A typical human erythrocyte has a disk diameter of approximately 6.2-8.2 μm and a thickness at the thickest point of 2-2.5 μm and a minimum thickness in the center of 0.8-1 μm, being much smaller than most other human cells. Leukocytes (white blood cells) include neutrophils (12-14 μm diameter), eosinophils (12-17 μm diameter), basophils (14-16 μm diameter), lymphocytes (average 6-9 μm in diameter for resting, and 10-14 μm diameter for activated), and monocytes, the largest type of white blood cells that can be up to 20 μm in diameter. As shown in FIG. 1, the size difference between CTCs and hematologic cells generally permits distinguishing CTCs from other cells in circulating blood (CTCs~9-20 μm; RBC~8 μm discoid; leukocytes~7-12 μm). See FIG. 1. Subsequent tumor cell specific labeling using antibodies (or cell-specific fragments thereof) or other tumor cell specific ligands increase the selectivity of the method.

Since CTCs are present as one in $10^6$-$10^7$ mononuclear cells in the bloodstream, high-sensitivity enrichment techniques are used that rely on immunological or morphological differences in CTCs from the blood cells. Immunological approaches often target epithelial cell surface markers (such as EpCAM) and tumor-specific proteins (such as Her2-neu, MUC I/MUC2, carcinoembryonic antigen (CEA), mammaglobulin, and alpha-fetoprotein) or aim to deplete CD45+ cells. Microfilters, density-gradient separations, and microfluidics platforms are examples of morphology-based methods. All of these approaches have inherent biases, suffer from low enrichment efficiencies and a significant number of CTCs may down-regulate surface antigens or exhibit varying morphological features. These biases pose a significant challenge in the field as it is still largely unknown which subset of CTCs are responsible for metastasis or are reliable prognostic markers. Thus, it is important to develop techniques that can ensure high sensitivity isolation of all candidate CTC sub-types to screen for the most clinically relevant candidates. The devices and methods described herein permit the isolation and enumeration of the CTC subtype of interest.

A combined enrichment method integrates both immunological and morphologic-based approaches to tag and isolate pure CTCs with less bias and based on tunable parameters. The method combines microfluidic intracellular delivery (FIG. 1) and antibody staining to yield robust, high sensitivity purification of circulating tumor cells from whole blood (FIG. 2) comprises a width from 4μ-10 μm, length of 1 μm-100 μm, and 1-10 constrictions in series. The estimated speed of the cells can range from 10 mm/s to 10 m/s. The specific device parameters chosen are dictated by the target tumor cell type, e.g., a different device design is used to select CTCs for a melanoma patient vs. a colon cancer patient. Examples of tumor cell sizes/diameters include; melanoma~15 um, colon cancer~11 um, and pancreatic cancer~15 um.

In this approach, a rapid mechanical deformation delivery system exploits the inherent size difference between many CTCs and the surrounding blood cells to selectively deliver fluorescent, magnetic and/or other distinguishing materials to the tumor cells. In further processing, antibody-based fluorescent and/or magnetic tagging is used to enhance the contrast between the candidate CTCs and the surrounding blood cells. By uniquely combining size-based and immunological approaches to CTC isolation, this technology has demonstrated utility for the non-biased isolation of candidate tumor cells from patient samples for analysis. In some implementations, both smaller and larger cells are deformed but the smaller cells membrane is not deformed to the point that the membrane becomes compromised. For example, to selectively delivering to 15 μm tumor cells in whole blood where most healthy white blood cells are ~8 μm in size, a 6 um width constriction can be used. Such a constriction would deform both cell types but would very preferentially disrupt the membrane of the 15 μm tumor cells not the 8 μm blood cells.

Clinical/Translation Relevance

CTCs are being explored as surrogates for tumor biopsies for understanding mechanisms of resistance and guiding the selection of targeted therapies. Measures of the number and composition of CTCs before and after treatment indicate treatment efficacy and prognosis. The approach utilizes a robust, high-throughput, disposable device for the tagging of CTCs based on cell size and surface antigens. Moreover, the ability to deliver a diversity of macromolecules also enables one to deliver molecular probes (such as antibodies, quantum dots, carbon nanotubes, and molecular beacons) that respond to the intracellular environment and thus provide further information on the intracellular properties of the target cell. This combinatorial approach provides a robust platform capable of enriching CTC populations that would have been missed by alternative methods that rely solely on immunological or morphological separation. The technique is useful to isolate patients' CTCs.

Example 1

Whole blood or other cell suspensions are processed using both unlabeled and/or antibody-coated magnetic beads. These cells are then isolated using a high-fidelity, magnetic enrichment system for rare cells. A nanowell technology may also be used to achieve high purity isolations by imaging and robotically-retrieving single cells of interest from an elastomeric array of 84,672 subnanoliter wells.

Obtaining single, live, pure, intact CTCs of diverse phenotypes allows a host of characterization efforts from the genomic to functional levels with immediate clinical and translational relevance. The methods permit a highly sensitive and specific enrichment of live, diverse CTCs with reduced bias.

Example 2

Magnetic nanoparticles are delivered to tumor cell lines & PBMCs. Nanoparticle delivery to EpCAM-expressing, epithelial cancer cell lines, e.g., HT-29, LNCaP, and SK-BR-3, is compared to bulk peripheral blood mononuclear cell (PBMC) suspensions derived from human blood.

10 nm iron-oxide nanoparticles with a polyethylene glycol (PEG) surface coating are delivered to cancer cells mixed with whole blood, and the resulting mixture of tagged cells are processed using the cell separation system described above. For example, the microfluidic delivery system was used to induce a rapid mechanical deformation of a cell to generate transient pores in the cell membrane (FIG. 1). The approach has demonstrated an ability to deliver a range of materials, including proteins, RNA, DNA and nanoparticles to a variety of cell types and works with whole blood, a medium that often poses problems for microfluidic systems.

Exemplary tagging molecules, e.g., 3 kDa and 70 kDa, fluorescently-labeled, dextran polymers as model molecules, were used to discriminate between PBMCs and two different cancer cell lines based on size alone. The results also indicate the utility of the system for the selective delivery of magnetic particles to tumor cells in the blood. PEG coated iron-oxide particles are used to magnetically tag colon cancer (e.g., as exemplified by the cell line HT-29). Further enrichment is accomplished using conjugation of FITC to the iron-oxide nanoparticle surface to directly measure nanoparticle uptake.

PEG coated 10 nm iron-oxide nanoparticles are delivered to cell suspensions that are suspected of containing or are known to contain CTCs, e.g., a patient-derived blood sample, or cell lines HT-29, LNCaP, and SK-BR-3 cells, separately mixed with whole blood. The resulting mixture of tagged cells are then purified, e.g., using a high fidelity magnetic separator. The separator accurately discriminates between the model CTCs with high iron-oxide content and less-effectively labeled PBMCs. Optionally, red blood cells are lysed prior to treatment, nanoparticle concentration increased, their size altered, or incorporating multiple treatment steps.

Example 3

Figure 2:
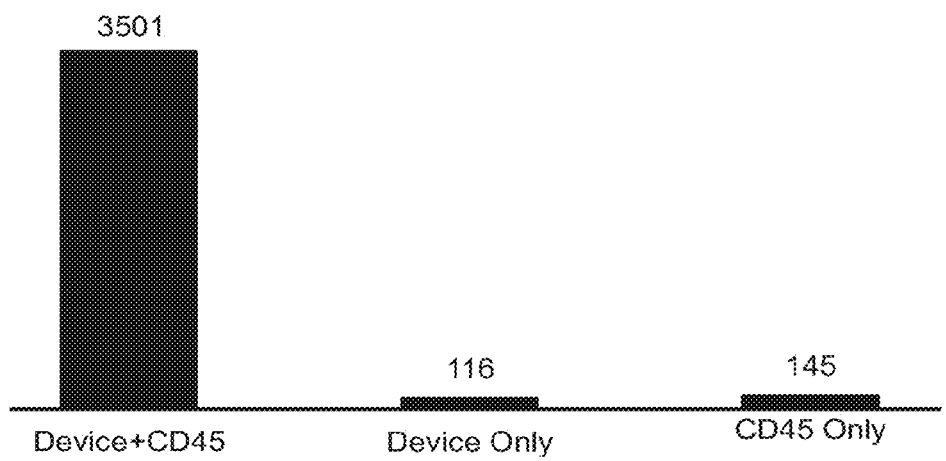
FIG. 2 is a bar graph showing that combining size selective delivery of the microfluidic platform with antibody staining for CD45 produces a sample enrichment factor over an order of magnitude better than either technique independently.
Figure 3A:
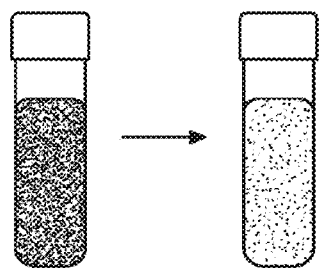
FIG. 3A is a schematic diagram of cell labeling. Red blood cells (RBCs) were depleted from whole blood by RBC lysis using standard erythrocyte lysis reagents such as eBioscience RBC lysis buffer (Cat. No. 00-4333). The resulting suspension flowed through the constriction channel microfluidics device incubated with a fluorescent dye (and optionally other compounds). The suspension was then labeled for CD45 and processed on a fluorescence-activated cell sorter (FACS) machine to collect the non-CD45+ cells that have been labeled with the fluorescent dye.
Figure 3A:
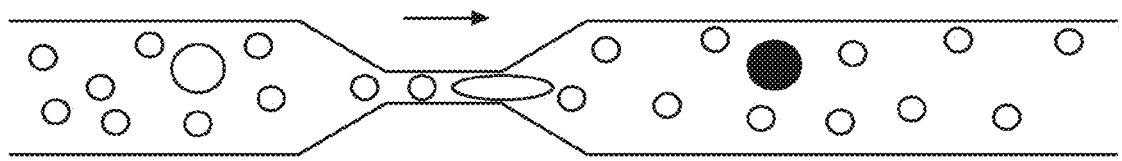
Figure 3A:
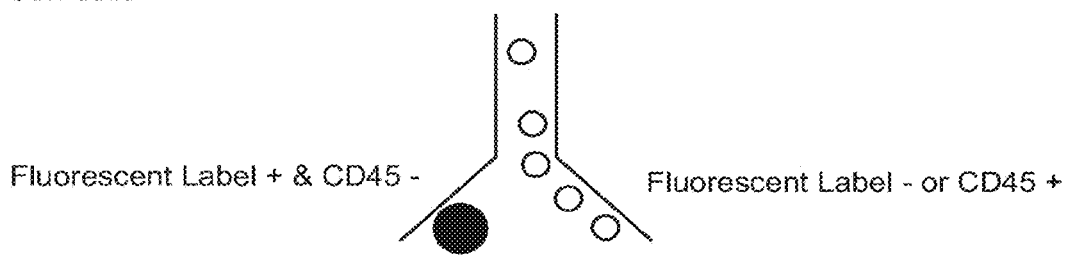
Figure 3B:
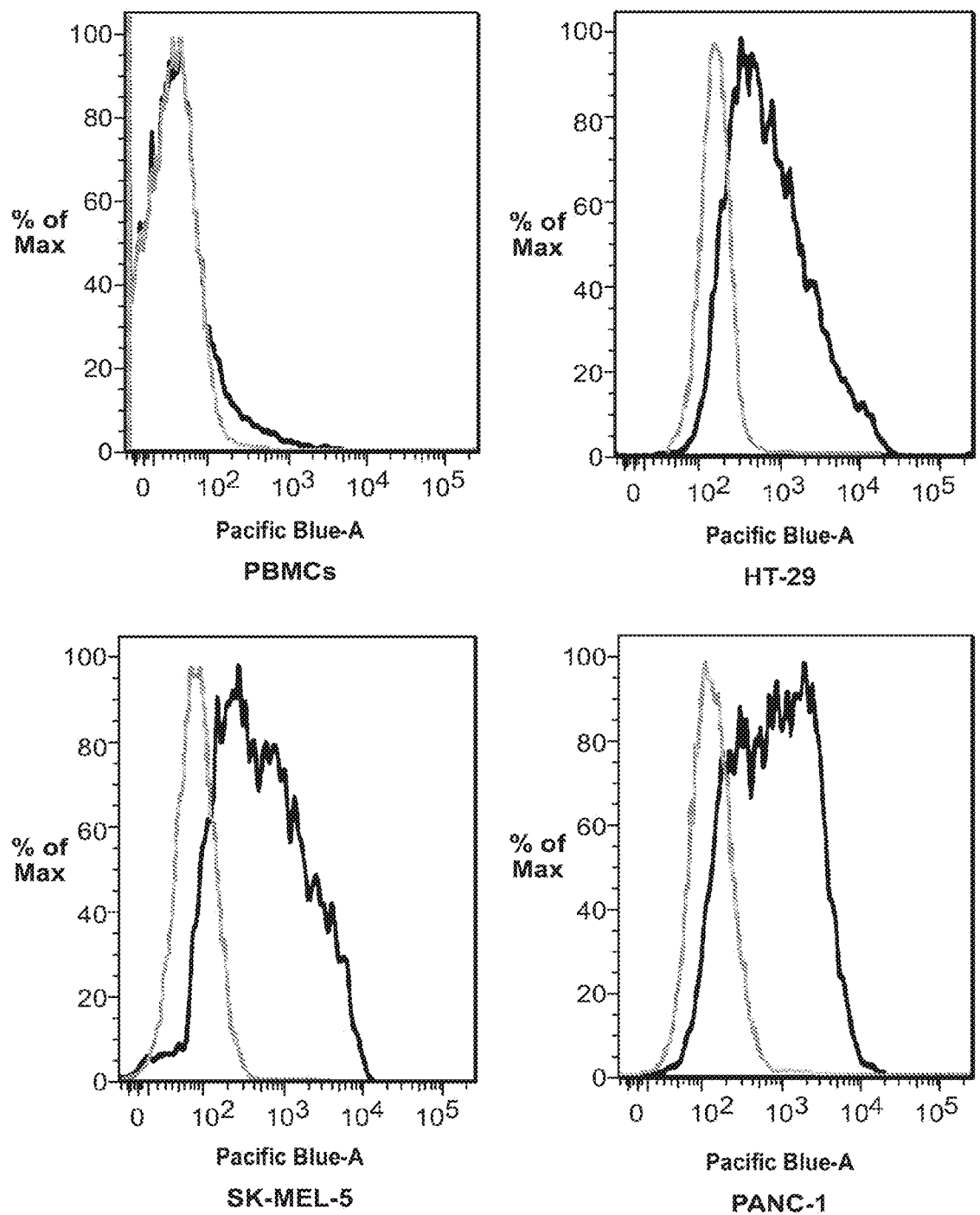
FIG. 3B is a series of flow cytometry plots of cascade blue conjugated 3 kDa dextran delivered by CellSqueeze devices to PBMCs (30-6 chip at 50 psi), HT-29 (30-6 chip at 50 psi), SK-MEL-5 (10-7 chip at 50 psi), and PANC-1 (10-7 chip at 50 psi).
Figure 3C:
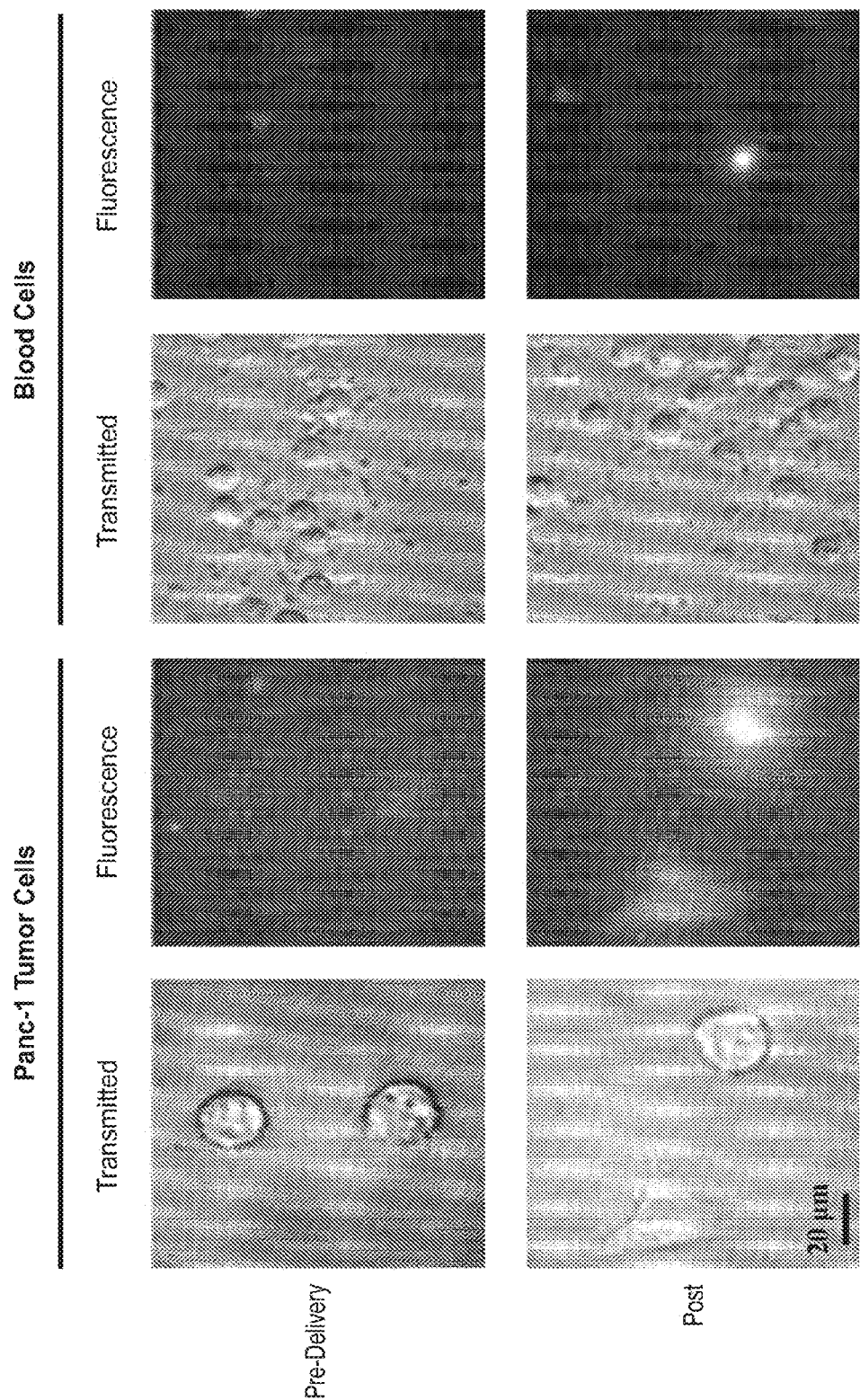
FIG. 3C is a series of transmitted light and fluorescence micrographs of Panc-1 tumor cells and blood cells before and after passing through the constriction channel. The pre-delivery cells are incubated in the presence of dye to correct for background endocytosis. The post-delivery images were taken 24 h after delivery to demonstrate retention of dye and ability of the cells to adhere and grow following delivery. Although large blood cells can also get labeled in the process, these data demonstrate selective labeling of tumor cells.
Figure 4:
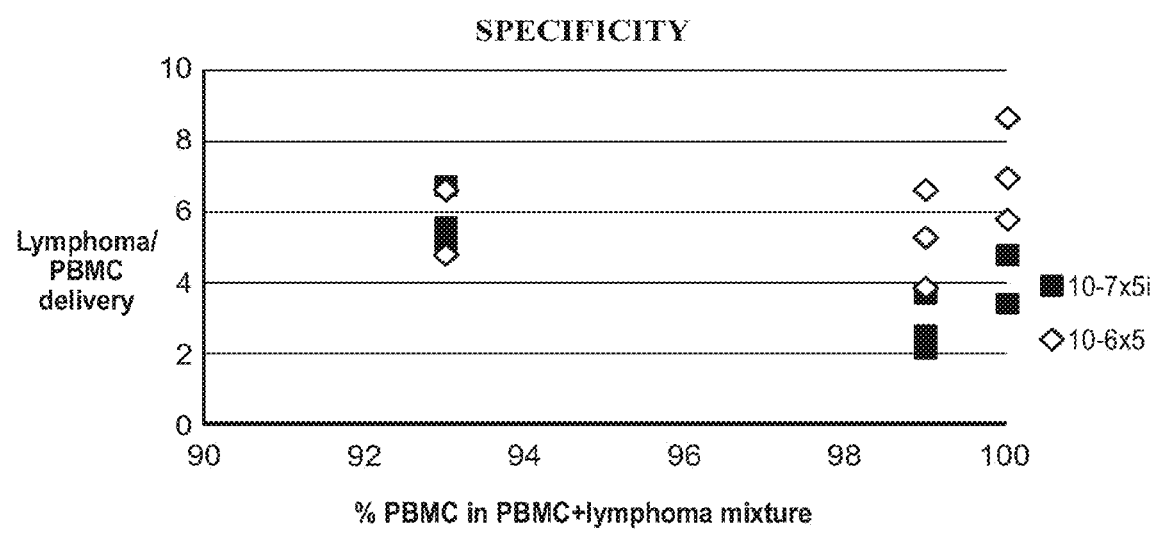
FIG. 4 is a plot of PBMC delivery versus percent PBMC in PBMC and lymphoma mixture showing selective delivery of dyes to lymphoma cells vs. healthy PBMCs. Even when the suspension is 99.9% healthy PBMCs by number, in some implementations up to 8 times specificity in delivery can be achieved. In other implementations, greater specificity can be achieved.
Figure 5A:
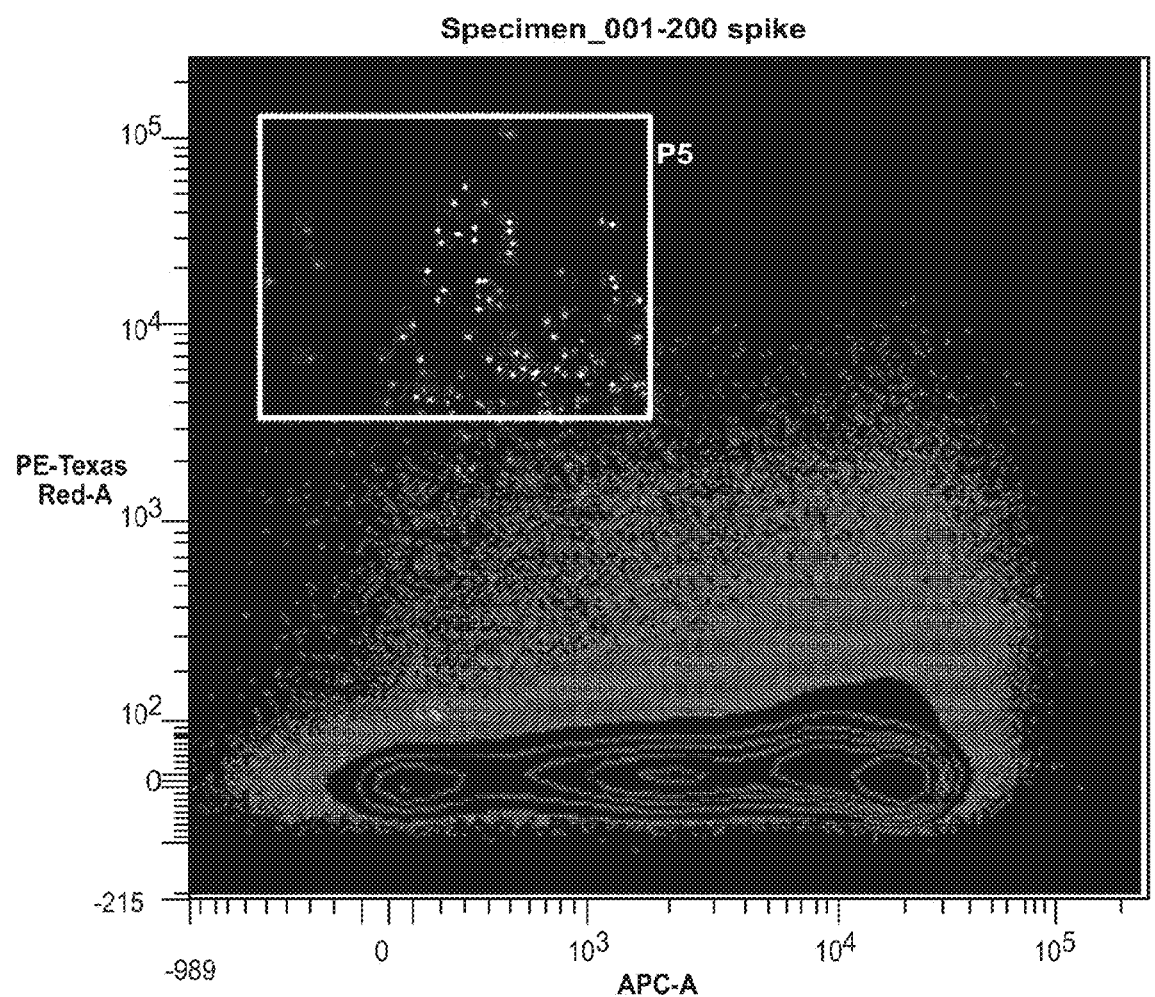
FIG. 5A is a FACS plot of tetramethylrhodamine dextran-labeled Panc-1-GFP cells spiked into whole blood (40 cells/ml) and processed with a CD45 counter stain (APC).
Figure 5B:
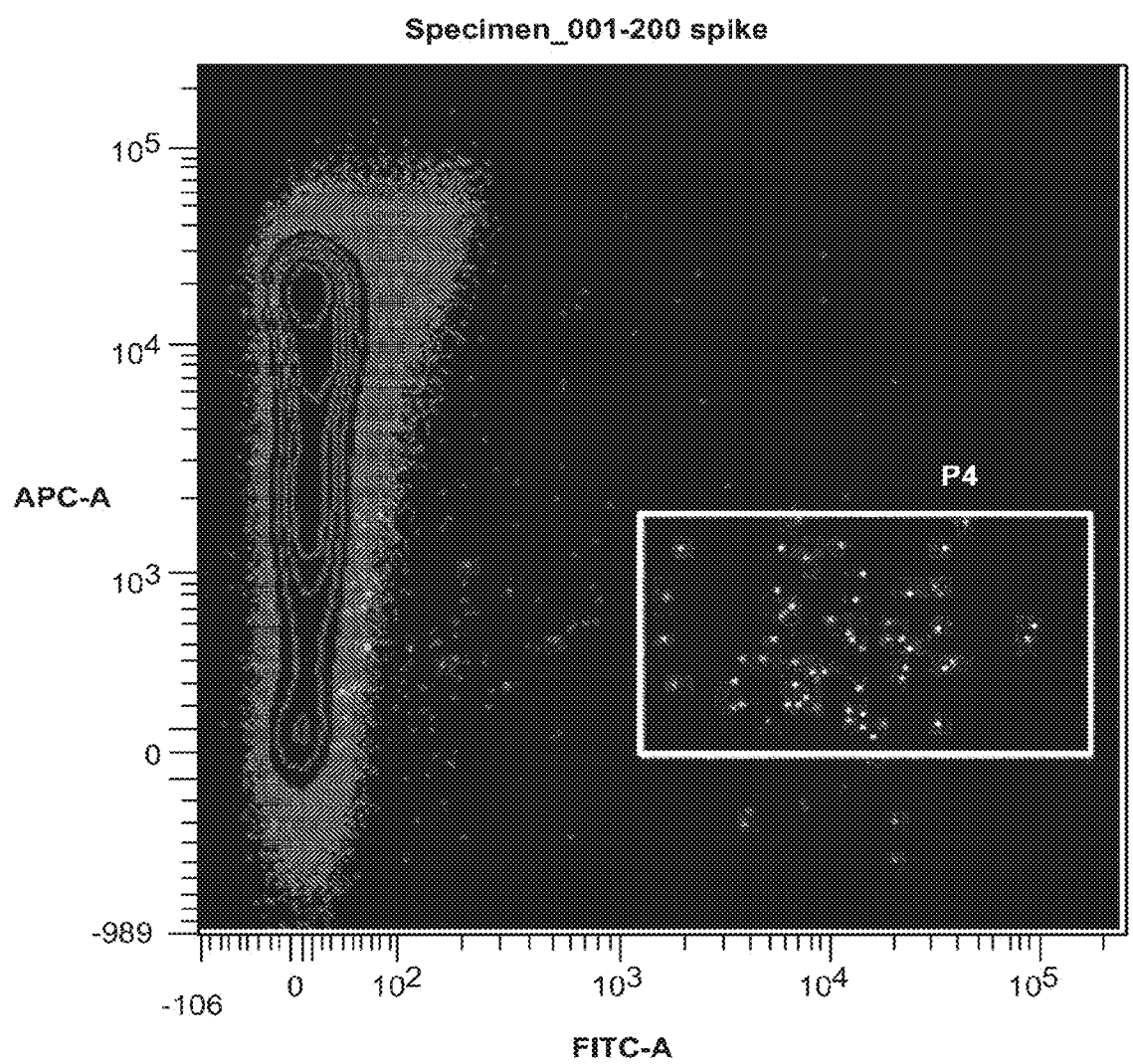
FIG. 5B is a FACS plot of GFP versus CD45, demonstrating how PANC-1 GFP tagging could be verified independently based on GFP fluorescence. The P5 gate would be used as a basis for sorting candidate CTCs, P4 is used to verify the identity of PANC-1 GFP cells. Green dots are accurate hits (P4 & P5), red dots are false positives (P5 only), blue dots are misses (P4 only).
Figure 5C:
FIG. 5C is an image of histopathology of HTB1760's primary tumor confirms pancreatic ductal adenocarcinoma.

A combined immunological and morphologic-based method is carried out as follows. After cell size-based processing by the device, cells are treated with an antibody or other tumor cell specific ligand such as fluorescently labeled anti-CD45 antibodies. The sensitivity and specificity of three different separation approaches were compared: 1) device only 2) anti-CD45 antibody only 3) device+anti-CD45 antibody. Morphologic tagging (device)+immunological tagging (e.g., anti-CD45 antibodies) was found to show superior sensitivity (and specificity) relative to either of the individual techniques (FIG. 2). For example, a 2-5× increase in sensitivity and/or a 2-5× increase in specificity relative to anti-CD45 antibodies alone is observed. Enrichment factor of over an order of magnitude was observed (FIG. 2).

Example 4

In one example, the devices are fabricated out of silicon and glass. Alternatively, the device is fabricated using a polymer such as silicone, PDMS, polycarbonate, acrylic, polypropylene, polystyrene. Either device is sterilized (heat or gamma radiation) and disposable. Performance of the devices is validated for various cell types using materials and parameters. For example, performance at a range of flow speeds (100 mm/s-10,000 mm/s) using PEG coated quantum dots (ranging from 10-50 nm in size) is used to determine if the delivery efficiency of nanoparticles and cell viability. Exemplary device are described in PCT/US2012/060646, hereby incorporated by reference.

Advantages

When compared to existing approaches this method has the following advantages. Relative to antibody-based methods, this approach provides a non-biased isolation procedure that is generalizable to most cancer types and is independent of any particular cell surface marker. The device and method accomplishes the identification of CTCs that could not be isolated by existing markers and thus, has significant diagnostic and prognostic implications.

Relative to existing size-based isolation methods, the device and methods described herein provide far higher throughput and are tunable by varying "W" (FIG. 1) to capture specific CTC size ranges. For example, a 6 µm width constriction is suitable for the capture of colon cancer cells whereas a 7 µm, and 8 µm width are suitable for the capture of pancreatic cancer and melanoma cells respectively. Moreover, unlike existing technologies, this system is combined with antibody-based technologies to enhance isolation sensitivity and/or enable multi-parametric isolation of subsets of CTCs (for example by isolating CTCs of a certain size+surface marker).

By enabling the effective, robust isolation of CTCs from a range of cancer types this technology would be a valuable platform in the fight against cancer. The prognostic and diagnostic potential of this technology could enable the identification of new genes that are critical to cancer progression and thus enable the development of novel therapeutics. It may also provide a more accurate prediction of patient life-expectancy and treatment efficacy.

The CTC isolation methods described herein combines immunological and size-based isolation to yield a high enrichment factor/recovery rate and adjustable bias (marker specific vs. size specific).

Although a few variations have been described in detail above, other modifications are possible. For example, the implementations described above can be directed to various combinations and subcombinations of the disclosed features and/or combinations and subcombinations of several further features disclosed above. In addition, the logic flows described herein do not require the particular order described, or sequential order, to achieve desirable results. Other embodiments may be within the scope of the following claims.

The invention claimed is:

1. A method for delivering a compound into a cell based on a physical property of the cell comprising:
providing a cell suspension comprising a first group of cells and a second group of cells, wherein the first group of cells have a relatively different size, diameter, and/or membrane stiffness than the second group of cells;
passing the cell suspension through and out of a microfluidic channel that includes a constriction, wherein, as the cell suspension passes through the microfluidic channel, the constriction induces greater disruption to a cell membrane of the first group of cells as compared to a cell membrane of the second group of cells, such that a greater amount of the compound enters the first group of cells through the disruptions as compared to the second group of cells when the first group of cells and the second group of cells are contacted with the compound; and
contacting the cell suspension with the compound.

2. The method of claim 1, wherein the first group of cells have a different size than the second group of cells.

3. The method of claim 1, wherein the first group of cells have a relatively different diameter than the second group of cells.

4. The method of claim 1, wherein the constriction has a diameter smaller than the size of cell in the cell suspension to which the compound is delivered.

5. The method of claim 1, wherein the constriction has a diameter smaller than the size of the smallest cell of the first group of cells or the smallest cell of the second group of cells.

6. The method of claim 1, wherein the constriction has a diameter smaller than the size of the largest cell of the first group of cells or the second group of cells.

7. The method of claim 1, wherein the cell suspension is contacted with the compound after the suspension is passed through the microfluidic channel comprising the constriction.

8. The method of claim 1, wherein the cell suspension comprises whole blood.

9. The method of claim 1, wherein the cell suspension comprises peripheral blood mononuclear cells (PBMCs).

10. The method of claim 1, wherein the cell suspension comprises an erythrocycte-depleted population of peripheral blood cells.

11. The method of claim 1, wherein the compound has a molecular mass of 0.5 kDa to 5 MDa or a molecular mass of 3 kDa to 10 kDa.

12. The method of claim 1, wherein the compound comprises one or more of a protein, a nucleic acid, a detectable marker, an active biomolecule, and a toxin.

13. The method of claim 1, wherein the compound comprises a detectable marker.

14. The method of claim 1, wherein:
(a) the constriction has a width from 4 µm-10 µm;
(b) the constriction has a length of 1 µm-100 µm; and/or
(c) the microfluidic channel has 1-10 constrictions in series.

15. The method of claim 1, wherein the cell suspension is passed through the microfluidic channel at a speed ranging from 10 mm/s to 10 m/s.

16. The method of claim 1, further comprising applying a pressure to the cell suspension to drive the cell suspension through the constriction of the microfluidic channel.

17. The method of claim 1, wherein the first group of cells and/or the second group of cells comprise a cell selected from the group consisting of: tumor cells, PBMCs, and erythrocytes.

18. The method of claim 17, wherein the first group of cells are PBMCs.

19. The method of claim 18, wherein the PBMCs comprise leukocytes.

20. The method of claim 19, wherein the leukocytes comprise neutrophils, eosinophils, basophils, lymphocytes, and/or monocytes.

21. The method of claim 20, wherein the leukocytes are lymphocytes.

* * * * *

UNITED STATES PATENT AND TRADEMARK OFFICE
CERTIFICATE OF CORRECTION

PATENT NO. : 11,806,714 B2
APPLICATION NO. : 17/075116
DATED : November 7, 2023
INVENTOR(S) : Armon R. Sharei et al.

It is certified that error appears in the above-identified patent and that said Letters Patent is hereby corrected as shown below:

In the Specification

At Column 1, Lines 21-24, in the paragraph under the heading "GOVERNMENT SUPPORT":
"This invention was made with Government support under Grant Nos. R01 GM101420, P30 CA014051, and EB011187 awarded by the National Institutes of Health. The Government has certain rights in the invention."

Should be:
--This invention was made with government support under CA014051, EB011187, and GM101420 awarded by the National Institutes of Health. The government has certain rights in the invention.--

In the Claims

At Column 10, Claim 1, Line 1:
"group of cells have a relatively different size"

Should be:
--group of cells have a different size--

At Column 10, Claim 3, Lines 18-20:
"The method of claim 1, wherein the first group of cells have a relatively different diameter than the second group of cells."

Should be:
--The method of claim 1, wherein the first group of cells have a different diameter than the second group of cells.--

Signed and Sealed this
Seventh Day of May, 2024

*Katherine Kelly Vidal*
Katherine Kelly Vidal
*Director of the United States Patent and Trademark Office*